United States Patent

Cannon et al.

[11] 4,134,997
[45] * Jan. 16, 1979

[54] EFFECT OF AN AMINOTETRALIN DERIVATIVE ON CORONARY BLOOD FLOW IN INFARCTED HEARTS

[75] Inventors: Joseph G. Cannon; John P. Long; John N. Diana, all of Iowa City, Iowa

[73] Assignee: University of Iowa Research Foundation, Iowa City, Iowa

[*] Notice: The portion of the term of this patent subsequent to Feb. 4, 1992, has been disclaimed.

[21] Appl. No.: 773,353

[22] Filed: Mar. 1, 1977

[51] Int. Cl.² ........................................ A61K 31/135
[52] U.S. Cl. .................................................. 424/330
[58] Field of Search ........................ 424/330; 260/574

[56] References Cited

FOREIGN PATENT DOCUMENTS 2363535 6/1974 Fed. Rep. of Germany.

OTHER PUBLICATIONS

Cannon et al., J. Med. Chem., vol. 15, No. 4, pp. 348–350 (1972).
Sprehnger et al., J. Med. Chem., vol. 12, pp. 487–490 (1969).

*Primary Examiner*—Stanley J. Friedman
*Attorney, Agent, or Firm*—Beveridge, DeGrandi, Kline & Lunsford

[57] ABSTRACT

The compounds represented by the structural formulae:

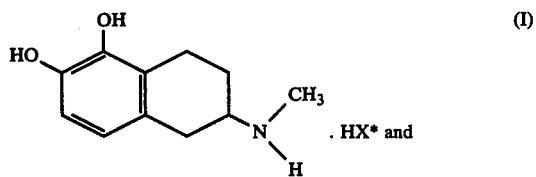

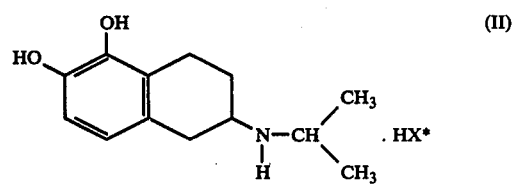

one each used for the treatment of warm blooded mammals with infarcted hearts.

The compounds I and II have a totally unpredictable effect on the infarcted heart. An artificial infarct (stoppage of blood vessel) is produced, to mimic the occurrence of a heart attack. Administration of a suitable amount of the compound opens new blood channels in the heart tissue, by-passing the infarcted region, and providing a supply of arterial blood to the area served by the occluded blood vessel. The necrosis which normally occurs in regions of the heart muscle as a result of a stoppage of an artery and resultant oxygen deficiency is largely prevented.

6 Claims, No Drawings

EFFECT OF AN AMINOTETRALIN DERIVATIVE ON CORONARY BLOOD FLOW IN INFARCTED HEARTS

The invention described herein was made in the course of work under a grant or award from the Department of Health, Education and Welfare.

The present invention pertains to the treatment of a patient; viz a mammal, with an infarcted heart.

Ischemic injury to the myocardium is a complex biological situation not only at the local level where cellular and tissue events have not been clearly assessed and functionally correlated, but also for the organism as a whole where myocardial damage can compromise activity or cause death. In the most fundamental sense, the lack of blood flow and thus oxygen delivery insufficient to meet tissue oxygen demands and removal of metabolic waste products is the predominant factor in the genesis of tissue injury and malfunction of the myocardium.

The present invention relates to the use of two compounds; viz (I) 5,6-dihydroxy 2-methylaminotetralin hydrobromide and (II) 5,6-dihydroxy-2 isopropylaminotetetalin hydrobromide and their use as coronary vascular vasodilator agents.

The compounds used in accordance with the present invention are represented by the following structural formulae:

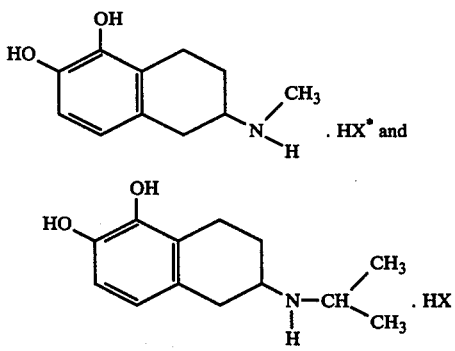

The compound 5,6-dihydroxy 2-methylaminotetralin hydrobromide is known in the art. The isopropyl compound is described in a copending application Ser. No. 646,300 filed Jan. 2, 1976 the entire disclosure of which is relied on in this respect and is incorporated by reference herein.

\* $X = Cl^-, Br^-, I^-, NO_3^-, SO_4^{--}, PO_4^{---}$, tartrate or other organic acid anion.

SUMMARY OF THE INVENTION

In accordance with the method of treating mammals with an infarcted heart, it has been determined that the compounds described above actually induce new circulatory pathways in the heart to open up, bypassing the plugged region of the coronary vessel, and supplying blood to the affected area of the heart muscle.

DETAILED DESCRIPTION OF THE INVENTION

The present invention relates to the use of two aminotetralin derivatives as potent coronary vasodilator agents. This is evidenced by the fact that blood flow to the normal heart was increased by approximately 50% during an intravenous infusion according to the invention (10 μg × Kg$^{-1}$ × min$^{-1}$) and the increase in blood flow was distributed equally to all parts of the left ventricle, right ventricle and septum. Coronary vascular resistance descreased by approximately 50%. Further evidence to support this is that the permeability surface area product for transcapillary exchange of lipid insoluble substances fructose and glucose was increased between 10% and 20% during intravenous administration of this agent. Together these observations indicate that the compounds can produce a pronounced vascular dilatation in the normal mammalian heart as well as increase the capillary surface area available for exchange of substances.

In the experiments, dog hearts were subjected to acute, sudden, occlusion of a portion of the left anterior descending branch of the left coronary artery. Use of the compounds according to the invention causes a significant increase in blood flow to both normal myocardium and ischemic myocardium. The increase in blood flow to normal tissue of the infarcted dog heart may be increased by 60%-70% over post-occlusion flow values. Blood flow in ischemic myocardium may be increased by 70% over post-occlusion values. Coronary vascular resistance, for the whole heart, which had a value of 1.59 ml × min$^{-1}$ × mmHg$^{-1}$ following coronary occlusion decreases to 1.15 ml × min$^{-1}$ × 100 g$^{-1}$ during intravenous infusion of the compound according to the invention. These data show that the compounds according to the invention are effective in producing coronary vascular vasodilation in the infarcted dog heart and that such vasodilator activity apparently opens up existing collateral blood channels so that flow to that tissue which had been served by the occluded branches of the LAD can now receive a greater increment of blood flow. This last observation is of critical importance since adequate blood flow, thus oxygen delivery and metabolic waste product removal, is critical for normal myocardial function. The ability to produce blood flow to a portion of the heart made ischemic by coronary artery occlusion by a pharmacologic agent has not previously been reported. It is known that several pharmacologic agents such as nitroglycerin, propranolol, practolol and minoxidil tend to reduce the extent of myocardial damage subsequent to acute myocardial infarction, but there is no evidence that these agents promote blood flow to ischemic myocardium. Since myocardial function in marginally ischemic tissue is improved with these agents it is thought that blood flow to marginally ischemic zones may be improved. There remains many unanswered questions about the mechanism and factors which will salvage marginally ischemic or ischemic tissue in the acutely infarcted myocardium. Still, it is without question that the ability to increase blood flow to ischemic tissue is the first step toward substrate delivery which will increase tissue survival.

The marked increase in blood flow to normal and ischemic myocardium and the vasodilator properties of the compounds I and II described above on the coronary vasculature can be more readily appreciated when it is remembered that compound I caused peripheral vasodilation and a decrease in aortic diastolic pressure of from 20-25 mmHg below control when blood flows were determined. Despite the marked decrease in driving pressure for coronary flow, myocardial vascular resistance was decreased in sufficient magnitude to cause large increases in myocardial blood flow. When a second infusion of compound I was administered (approximately 5-10 minutes after the first infusion) there were further increases in blood flow and decreases in coronary vascular resistance. For the second dose of I these changes were augmented by an increase in aortic diastolic pressure. It is of some interest to note that despite the marked decrease in mean aortic pressure, which would normally elicit a reflex tachycardia heart rate did not increase during administration of compound I.

The compounds I and II appear to have physiologic effects which are of a classic nature for an anti-anginal agent. They have a potent coronary vasodilator effect thus increasing blood flow to ischemic myocardium which is presumed to be the major cause of angina. They produce a reduction in heart rate, at low doses, thus reducing the amount of oxygen needed by the myocardium to function as an effective pump. With low doses there is a peripheral vasodilation and reduction in aortic pressure or after load against which the heart must pump again reducing the work and the oxygen needed to produce adequate cardiac output. This latter action is similar to that produced by nitroglycerin which is an effective anti-anginal agent. The partial inhibition of adrenergic neural activity may be of significance in opposing the positive inotropic and chronotropic effects of increased sympatho-adrenal medullary discharge as occurs with fright, anxiety, etc. in association with an anginal attack. Compounds I and II do not appear to compromise cardiac output since evidence shows no change or a slight increase.

In the anesthetized (sodium pentobarbital), open chest dog an intravenous infusion (10 $\mu$g $\times$ min$^{-1}$ $\times$ Kg dog weight$^{-1}$) of the compounds I and II are capable of producing the following physiologic actions.

1. An increase in blood flow to normal myocardium which was 60-70% above control values.
2. An increase in blood flow (60-70% above control) to both normal, marginally ischemic, and ischemic tissue of the heart when a portion of the LAD branch of the left coronary artery was completely occluded with a ligature.
3. A 50% to 60% reduction in coronary vascular resistance for the whole heart in both the normal (non-infarcted) and infarcted myocardium.
4. For the normal (control) heart there was no selective increase in epicardial blood flow since the endo/epi blood flow ratios remained close to 1.0.
5. In the infarcted dog heart the compound produced an increase in flow to all areas but there appeared, when blood flow exceeded 100% of control values, to be an increased distribution to the epicardial surface as indicated by a decrease in the endo/epi blood flow ratio from 1.04 to 0.89.
6. The compound increased the capillary surface area available for exchange of substances as indicated by a 15%-30% increase in capillary permeability-surface area products for fructose and sucrose.
7. The following hemodynamic effects were observed during compound infusion:
   a. Decreased mean aortic pressure
   b. A transient decrease in LVESP associated with the decrease in aortic pressure and no change in LVEDP.
   c. No change in heart rate.
   d. No change in left ventricular dp/dt.
   e. No change in central venous pressure.
8. The cardiovascular actions of the compounds increase flood flow and oxygen delivery to the myocardium while decreasing the work and oxygen utilization by the heart suggesting it may be a potent anti-anginal agent.
9. By opening up existing collateral channels, the compounds provide blood flow to areas of the myocardium which were either devoid of or had little blood flow from occlusion of a large feeder artery. Because of this ability of this agent to aid in survival of marginally ischemic myocardium and/or ischemic myocardium thus preventing the loss or enlargement of non-functional myocardium following coronary artery obstruction it is of great practical importance in health care.

Examples

Experiments were performed on mongrel dogs without regard to sex or species. All dogs were anesthetized with sodium pentobarbital (30 mg/kg body weight) before experimentation. In the following the HBr salt was used, X = Br.

In preparation for the measurements to be reported, the dogs were respirated using positive pressure and room air and the heart was exposed by performing a midline incision in the chest. After pericardectomy, catheters were placed in the left atrium for injection of radioactive microspheres (7-9$\mu$ diameter), and in the left ventricle (via the left atrium) for measurement of ventricular pressure. Catheters were also placed in the arch of the aorta (via the femoral artery) for withdrawal of reference samples; in the inferior vena cava for measurement of central venous pressure; and in the arch of the aorta for measurement of aortic pressure. Electrocardiographic tracings were obtained for most animals.

Unless otherwise specified, all values presented are satistically significant at the 95% confidence level.

Table 1 presents the effect of compound I, 5,6-dihydroxy 2-methylaminotetralin hydrobromide, on blood flow to the left ventricle, right ventricle and septum of the dog in the control state. The agent was administered by a continuous intravenous infusion in a dose of approximately 10 $\mu$g/kg body wt/min (range 8.5 to 13.9 $\mu$g/kg body wt/min) in all work done herein.

TABLE I

| Anatomical Segment | Number | Coronary blood flow (ml $\times$ min$^{-1}$ $\times$ 100g$^{-1}$) Control | Compound I | % Change |
|---|---|---|---|---|
| Left ventricle | N = 10 | 97.9 ± 11.5 | 151.8 ± 17.9 | + 55.1 |
| Septum | N = 10 | 97.5 ± 19.0 | 137.2 ± 26.7 | + 40.7 |
| Right ventricle | N = 10 | 76.9 ± 17.4 | 126.6 ± 28.7 | + 64.6 |
| Whole heart | N = 10 | 93.2 ± 8.5 | 142.9 ± 13.0 | + 53.3 |

All values ± SE of the mean.
Note. For control flow values mean aortic pressure was 91.0 ± 11.3 mmHg. For compound I flow values, mean aortic pressure was 69.3 ± 16.7 mmHg.

The data in Table I demonstrate a substantial increase ($\approx$54%) in flow despite a 24% reduction in aortic pressure which resulted from peripheral vasodilatation. Heart rate was unaffected by compound I control value being 132 ± 14 bts/min and during compound I infusion 126 ± 18 bts/min (average values for 10 experiments).

Table II data are presented on the distribution of blood flow to the endocardium and epicardium for the same 10 experimental animals shown in Table I. These data are mean values for 40 pieces of heart tissue (left ventricular free wall 24 pieces, septum 9 pieces, right ventricle 7 pieces). Each piece of tissue was then further subdivided into endocardium, midwall and epicardium for a total of 120 segments of myocardium.

TABLE II

| Anatomical Segment | Coronary blood flow (ml $\times$ min$^{-1}$ $\times$ 100g$^{-1}$) | | | | | | % Change | |
|---|---|---|---|---|---|---|---|---|
| | Control | | | Drug | | | | |
| | ENDO | EPI | ENDO EPI | ENDO | EPI | ENDO EPI | ENDO | EPI |
| Left Ventricle | 95.2 ± 19.7 | 104.0 ± 21.5 | .92 | 150.7 ± 31.2 | 158.7 ± 32.9 | .95 | + 58.3 | + 52.6 |
| Septum | 98.8 ± 34.6 | 90.9 ± 31.9 | 1.09 | 135.4 ± 37.4 | 137.0 ± 47.7 | 1.00 | + 37.0 | + 50.7 |
| Right Ventricle | 77.0 ± 25.4 | 76.7 ± 25.3 | 1.00 | 127.4 ± 42.0 | 125.8 ± 41.5 | 1.01 | + 65.4 | + 64.0 |

All values ± SE of the mean.

These data demonstrate that flow was uniformly increased through out the entire myocardium and there was no evidence that the epicardium received more of the increased blood flow, or alternatively, that the endocardium received less of the increased blood flow.

To produce a myocardial infarction, a portion of the left anterior descending branch of the left coronary artery was exposed, isolated and a ligature securely tied around it to produce total occlusion of blood flow through the segment. The time and sequence of the experimental procedure was as follows: (1) Determination of control blood flow with tracer #1; (2) Occlusion of the coronary artery; (3) 45 min post-occlusion, determination of regional myocardial blood flow with tracer #2; (4) 50 min post-occlusion, infusion of compound I; (5) 55 min post-occlusion, determination of regional myocardial blood flow with tracer #3; (6) 60 min post-occlusion, begin 2nd infusion of compound I; (7) 65 min post-occlusion, determination of regional myocardial blood flow. The results of these studies are summarized in Table III.

reduced to 1.15. Clearly, a comparison of the values shows that blood flow increased more than could be attributed to the increase in pressure alone since aortic pressure during compound I was at the control value. This is further substantiated by the fact that, after the second infusion of compound I, blood flow increased to approximately 131% above the value for flow in the infarcted heart. The resistance for the whole heart after the second dose was 0.89 mmHg $\times$ ml per min$^{-1}$ $\times$ 100 grams$^{-1}$. Aortic pressure, during the second infusion of compound I, was at a value of 115 mmHg which was 7% above the control [pre-compound I(2)] value, yet blood flow increased by almost 65%. Again this would demonstrate a pronounced vasodilation of the coronary vascular bed.

Perhaps the most significant meaningful example of the coronary vasodilator effect of compound I is presented in Table IV. In this table those segments of the heart which were made ischemic by the occlusive procedure have been separated from the rest of the myocardial (non-ischemic) tissue. An arbitrary decision was

TABLE III

| Anatomical Segment | Coronary blood flow (ml $\times$ min$^{-1}$ $\times$ 100g$^{-1}$) | | | | | % Change | |
|---|---|---|---|---|---|---|---|
| | Control | Infarct | % Change | Compound I (1) | Compound I (2) | Compound I (1) | Compound I (2) |
| Left Ventricle | 92.1 ± 10.8 | 57.8 ± 6.8 | − 37.2 | 99.5 ± 11.7 | 134.9 ± 15.9 | + 72.1 | + 133.4 |
| Septum | 97.1 ± 18.9 | 69.3 ± 13.5 | − 28.6 | 112.1 ± 21.8 | 144.0 ± 28.0 | + 61.8 | + 107.8 |
| Right Ventricle | 60.7 ± 13.8 | 40.4 ± 9.2 | − 33.4 | 63.7 ± 14.4 | 101.5 ± 23.0 | + 57.7 | + 151.2 |
| Whole Heart | 85.4 ± 7.8 | 55.8 ± 5.1 | − 34.7 | 93.3 ± 8.5 | 128.5 ± 11.7 | + 67.2 | + 130.3 |

Values ± SE of the mean. N = 8 for all experiments except compound I (2) where N = 5.

These data demonstrate that, in our experimental procedure, production of an infarct reduced coronary blood flow by approximately 32% below control values. This was associated with a decrease in mean aortic pressure (presumably the result of decreased cardiac output) from 107.5 mmHg to 88.9 mmHg. Compound I increased blood flow, after infarction, by approximately 65%. Mean aortic pressure during compound I infusion was at the control value of 107.1 (presumably the result of increased cardiac output). The increase in flow cannot be attributed to the increase in aortic pressure alone although it must be a component in the response. This statement is made on the basis of calculated resistance was flow in the whole heart. In the control state of the calculated resistance was 1.26 mmHg $\times$ ml per min$^{-1}$ $\times$ 100 grams$^{-1}$; in the infarcted heart the resistance value was 1.59 and after compound I (1) the value was made that in any segment where blood flow was reduced by 60% or more below the control (pre-occlusion) values would be classified as ischemic. In eight experiments this represented 20% of the whole heart, i.e., ligation of a portion of the LAD produced ischemia in 20% of the myocardium. For any given heart there was variability in flow to discrete segments making up this 20% of ischemic myocardium with a range of 0.0 to 47.6 ml $\times$ min$^{-1}$ $\times$ 100 grams$^{-1}$.

TABLE IV

| Myocardial blood flow ml $\times$ min$^{-1}$ $\times$ 100g$^{-1}$ | | | | | % Change | |
|---|---|---|---|---|---|---|
| Control | Infarct | % Change | Compound I (1) | Compound I (2) | Compound I (1) | Compound I (2) |
| 88.8 ± 13.7 | 36.2 ± 6.8 | − 59.2 | 70.4 ± 19.5 | 95.7 ± 28.3 | 94.5 | 164.4 |

All values ± SE of the mean. N = 8.

The data in Table IV demonstrate that prior to coronary artery occlusion the average flow in those segments which ultimately became ischemic from the occlusive procedure averaged approximately 90 ml $\times$ min$^{-1}$ $\times$ 100g$^{-1}$. Subsequent to occlusion the flow was reduced in these segments to an average of 36 ml $\times$ min$^{-1}$ $\times$ 100g$^{-1}$. Administration of the first dose of compound I increased the flow to the ischemic segments by 95% and the second does of increased flow by 165% of the value which obtained during ischemia. That is, in the ischemic tissue, blood flow was brought back to approximately control (non-ischemic) values by the first dose of compound I and blood flow exceeded control (non-ischemic) values after the second dose.

For experiments with compound I, 5,6,dihydroxy 2-methylaminotetralin was administered intravenously at a rate of approximately 10 μg/kg dog weight per minute (range 8.5–13.9). Compound II may be administered in the same way using the same procedures with comparable results.

The pharmaceutical compositions of this invention will contain the active compound together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier than the pharmaceutical composition is administered intravenously. Saline solutions and aqueous dextrose and glycerole solutions can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the host. While intravenous injection is a very effective form of administration, other modes can be employed.

We claim:

1. A method for increasing the coronary blood flow in a warm blooded mammal comprising introducing into the blood stream of said mammal an amount of a compound selected from the group consisting of:

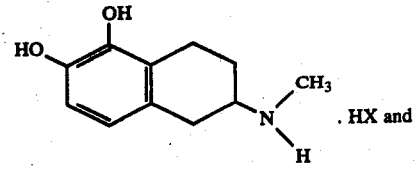

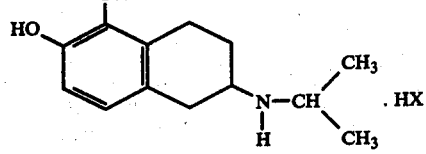

effective to produce the increased flow, X = Cl$^-$, Br$^-$, I$^-$, NO$_3^-$, SO$_4^{--}$, PO$_4^{---}$ tartrate or other organic acid anion.

2. The method of claim 1 wherein the amount is from 8.5 to 13.9 μg/kg body weight of mammal per minute.

3. The method of claim 1 wherein the compound is injected into the blood stream.

4. The method of claim 1 wherein X = Br.

5. A method of increasing the coronary blood flow in a warm blooded mammal with an infarcted heart comprising introducing into the blood stream of said mammal an amount of an active compound, effective to produce the increased flow, which is

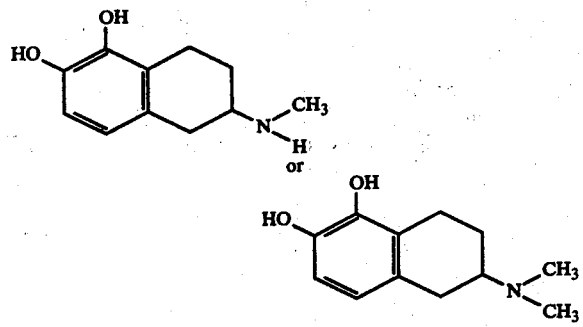

6. The method of claim 5 wherein the active compound is in the form of the hydrobromide salt.

* * * * *